United States Patent [19]  [11]  4,426,544
Carson  [45]  Jan. 17, 1984

[54] POWER RECOVERY IN MOTOR FUEL ALKYLATION PROCESS

[75] Inventor: Don B. Carson, Mt. Prospect, Ill.

[73] Assignee: UOP Inc., Des Plaines, Ill.

[21] Appl. No.: 394,376

[22] Filed: Jul. 1, 1982

[51] Int. Cl.³ .............................................. C07C 2/56
[52] U.S. Cl. .................................. 585/709; 585/723; 585/910; 585/913
[58] Field of Search ................ 585/910, 913, 709, 723

[56] References Cited

U.S. PATENT DOCUMENTS

| | | | |
|---|---|---|---|
| 3,012,082 | 12/1961 | Kelly et al. | 585/910 |
| 3,087,898 | 4/1963 | Pfeiffer et al. | 585/910 |
| 3,515,766 | 6/1970 | Root et al. | 585/910 |
| 4,144,281 | 3/1979 | Chapman et al. | 585/702 |
| 4,195,191 | 3/1980 | Boney | 585/706 |
| 4,249,030 | 2/1981 | Chapman et al. | 585/716 |

Primary Examiner—Curtis R. Davis
Attorney, Agent, or Firm—James R. Hoatson, Jr.; John F. Spears, Jr.; William H. Page, II

[57] ABSTRACT

An energy recovery method is disclosed for use on acid catalyzed alkylation processes which produce motor fuel blending components. The method is used on alkylation processes in which a light hydrocarbon, such as isobutane, is withdrawn from an elevated pressure fractionation column as a vapor-phase stream which is preferably a sidecut stream, condensed and then recycled to the reaction zone of the alkylation process. In the subject method, the vapor-phase stream is first depressurized to recover useful energy and is then condensed.

12 Claims, 1 Drawing Figure

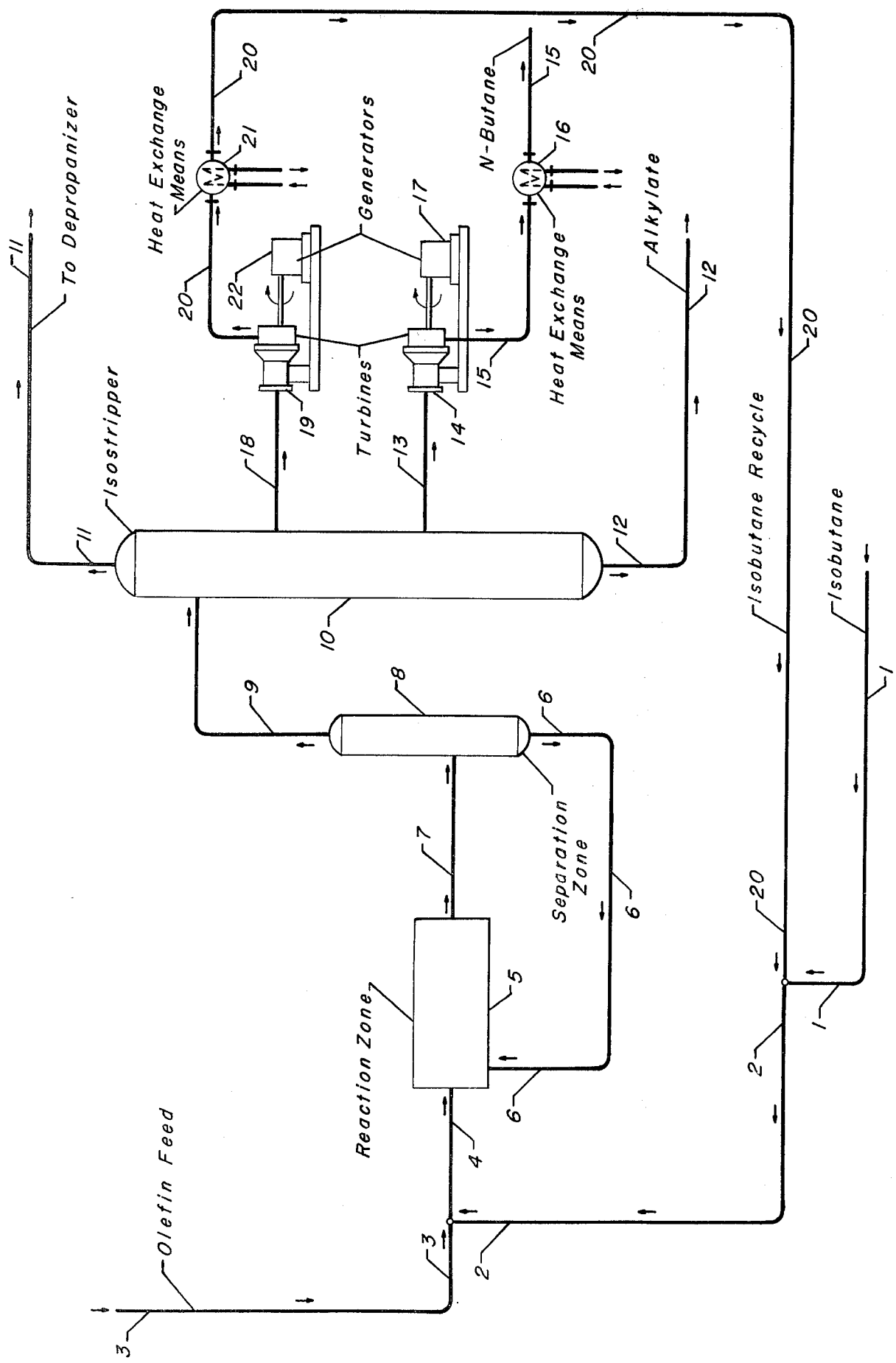

POWER RECOVERY IN MOTOR FUEL ALKYLATION PROCESS

FIELD OF THE INVENTION

The invention relates to a process for the production of motor fuel by the alkylation of light isoparaffinic hydrocarbons with light acyclic olefinic hydrocarbons. The invention is directed to an energy recovery method for use in an acid catalyzed process for the production of gasoline blending stocks by the reaction of isobutylene with isobutane. The invention is specifically directed to recovering energy available in a pressurized vapor-phase sidecut stream removed from a fractionation column used in the process, with the sidecut stream being condensed and preferably recycled to the reaction zone of the alkylation process.

PRIOR ART

Alkylation processes for producing motor fuels evolved from the efforts during World War II to produce additional amounts of high octane number gasoline. They have since come into widespread use in many petroleum refineries. Those skilled in the art of petroleum refining are therefore familiar with the overall design and operation of motor fuel alkylation processes.

Several different alkylation process designs are in widespread use. These different processes however often share several operating characteristics. For instance, the isoparaffinic and olefinic hydrocarbons are normally brought into contact with a substantial amount of liquid phase catalyst, often HF but possibly $H_2SO_4$, under liquid-phase conditions in an agitated reaction zone having cooling means or suitable heat sinks provided by subcooled process streams. The resultant mixture of hydrocarbons and the catalyst are then normally separated into separate liquid phases in a settling zone external to the reaction zone. The hydrocarbon phase is passed into fractionation facilities which recover any catalyst dissolved in the hydrocarbons, remove light hydrocarbons such as propane and produce an alkylate-containing product stream and an isoparaffin recycle stream. It is therefore known to recycle isoparaffin from the fractionation facilities to the reaction zone to improve the performance of the process.

U.S. Pat. No. 4,195,191 issued to W. G. Boney is pertinent for its general teaching of the process flow of a motor fuel alkylation process. In FIG. 1 of this patent there is illustrated the withdrawal from the isostripper 19 of an isobutane recycle stream carried by line 2. The isobutane recycle stream is removed as a sidecut and is eventually recycled to the reaction zone.

U.S. Pat. No. 4,144,281 issued to C. C. Chapman and P. D. Hann is pertinent for its showing of the use of an isobutane recycle stream in a motor fuel alkylation process which has a different overall process flow. In this proces the isobutane recycle stream is removed as the overhead stream of a fractionation column. The overhead vapors are compressed and then used to reboil an HF acid stripper.

U.S. Pat. No. 4,249,030, also issued to C. C. Chapman and P. D. Hann, is directed to an energy-efficient motor fuel alkylation process. This patent is pertinent for its showing of the passage of the isobutane recycle stream through an expander 16. However, it appears the isobutane recycle stream is cooled in three separate heat exchangers prior to entering the expander, and it is believed the isobutane enters the expander as a liquid. This belief is based in part on the teaching of lines 44 to 53 of column 2 of the patent.

BRIEF SUMMARY OF THE INVENTION

The invention provides a motor fuel alkylation process in which an increased amount of useful mechanical or electrical energy is recovered. The invention may allow a reduction in the overall utilities cost of operating the alkylation process or the production of electrical energy at no net increase in fuel consumption within the alkylation process. These features of the invention are achieved by recovering a portion of the potential energy present in a vapor-phase stream removed from the relatively high pressure deisobutanizer column of the alkylation process.

The invention may be broadly characterized as an alkylation process which comprises the steps of producing an alkylate hydrocarbon in a reaction zone by reacting a $C_6$-minus isoparaffinic hydrocarbon with an acyclic olefinic hydrocarbon in the presence of an acid catalyst; separating a process stream comprising the alkylate hydrocarbon and the isoparaffinic hydrocarbon in a fractionation column at a pressure above about 100 psig and thereby producing a net bottoms stream comprising the alkylate hydrocarbon and a vapor-phase stream which is rich in the isoparaffinic hydrocarbon; depressurizing the vapor-phase stream in a turbine and generating useful rotational energy; condensing the vapor-phase stream; and recycling at least a portion of the resultant condensate to the reaction zone.

BRIEF DESCRIPTION OF THE DRAWING

The Drawing presents a simplified process flow diagram illustrating the preferred embodiment of the invention. Various apparatus and associated process streams including fractionation column overhead condensing and reboiler means, vessel internals, acid regeneration facilities, HF stripping and depropanizer columns, etc., have not been shown as the inventive concept does not involve these elements of an alkylation process and they are subject to considerable variation.

Referring now to the Drawing, a first feed stream comprising isobutane enters the process via line 1 and is admixed with the liquid-phase isobutane recycle stream carried by line 20. The resultant combined isobutane stream is carried by line 2 to the junction with line 3 which carries a second feed stream comprising normal butenes. The isobutane and butene mixture is then passed through line 4 into the alkylation reaction zone 5 wherein it is intimately commingled with liquid-phase HF from line 6 at alkylation-promoting conditions. Preferably a hydrocarbon-HF emulsion is withdrawn from the reaction zone through line 7 and passed into a phase separation zone 8. Separate layers of the liquid HF and less dense hydrocarbons are formed in this zone, with the HF being recycled in line 6 and the hydrocarbons entering the isostripper column 10 through line 9.

The net hydrocarbon stream of line 9 comprises a product $C_8$ alkylate, unreacted isobutane, normal butane present in the feed streams, by-product propane and dissolved HF. This hydrocarbon stream enters near the top of the isostripper and is separated into several streams including a net overhead stream carried by line 11 comprising propane and HF which is directed to a depropanizer column. The alkylate hydrocarbons become concentrated in a net C<sub>5</sub>-plus bottoms stream carried by line 12.

Preferably two vapor-phase sidecut streams are removed from the isostripper. The lower sidecut stream carried by line 13 is rich in normal butane derived from the feed stream and/or a butane stream not shown which is also charged to the isostripper. This stream is depressurized in the turbine 14 which delivers rotational energy to the electrical generator 17. The butane-rich effluent of the turbine is then condensed in heat exchange means 16 and discharged from the process through line 15. In a similar manner an upper sidecut stream which is rich in isobutane is removed from the isostripper in line 18. This vapor-phase stream is passed through a power recovery turbine 19. The resultant low pressure stream is condensed in heat exchange means 21 and then returned to the reaction zone via line 20 as the isobutane recycle stream of the alkylation process. A pump not shown is required for this recycling. The energy recovered from the isobutane sidecut is transferred from the turbine 19 to an electrical generator 22.

DETAILED DESCRIPTION

The present high cost of all commercial forms of energy has prompted many developments in the areas of energy conservation. This has been especially true in the art of petroleum refining, which is a very energy-consuming industrial enterprise. However, despite conservation efforts large amounts of energy are not recovered in refineries. It is the objective of the subject invention to provide a method of recovering useful energy in an existing refinery alkylation process which requires little or no change in the operation of an alkylation unit. It is a further objective to provide a more energy-efficient method of recycling isobutane from a superatmospheric pressure fractionation column of an alkylation zone to the reactor of the alkylation zone. Other objectives of the invention are to provide an improved motor fuel alkylation process and to lower the utilities cost of operating a motor fuel alkylation process.

The use of the invention is not limited to any particular alkylation reactor configuration, catalyst or overall process configuration. The subject invention may therefore be applied to a wide variety of motor fuel alkylation processes. However, the invention is limited in its application to those alkylation processes in which a relatively volatile hydrocarbon is removed from a fractionation column as a vapor-phase stream which is at a substantial superatmospheric pressure and which is subsequently condensed. The relatively volatile hydrocarbon will preferably have less than six carbon atoms per molecule. More preferably this hydrocarbon has from three to five carbon atoms per molecule and is a saturated hydrocarbon. The vapor-phase stream may therefore be rich in propane, n-butane, isobutane and iso or normal amylene. The inventive concept may be applied to two or more streams, each of different composition, withdrawn from the same fractionation column as shown in the Drawing or from different fractionation columns in the same alkylation process. The inventive concept may also be applied to a column in an alkylation unit which is not functioning as an isostripper column. Further, the inventive concept may be applied in alkylation processes in which the hydrocarbon vapor stream is not removed as a sidecut stream. A minimum fractionation column pressure which depends on the specific circumstances of the individual alkylation unit is required to economically justify the use of the subject invention. Preferably the fractionation column is operated at a pressure above about 60 psig. More preferably the fractionation column is operated at a pressure above 100 psig, with yet higher pressures above about 150 psig being especially preferred. The pressure drop through the turbine is preferably greater than 75 psi.

In the subject process a pressurized vapor-phase stream is withdrawn from the fractionation column and depressurized in a power recovery or expansion turbine. The type of turbine, axial or radial flow, etc., is not a controlling factor and is chosen on the basis of cost and to optimize the performance of the process. The rotational energy delivered by the turbine is preferably transferred to an electrical generator to thereby generate electricity but could be employed in other ways such as driving a compressor or other moving equipment. After emerging from the turbine the depressurized vapors are condensed. This requires the cooling of vapors and may require more cooling than is required to condense the high pressure prior art vapor due to the reduced pressure. The temperature of the resultant condensate is not critical and is set by the temperature required for condensation and the desired recycle temperature of this stream. A condensate temperature of less than about 120° F. (49° C.) is preferred. An additional amount of energy over the prior art is also required to pump the resultant liquid back into the alkylation reactor, but these added energy requirements are more than offset by the energy recovered in the turbine.

A significant advantage of the inventive concept is that the available power delivered by the expansion turbine is produced without any additional heat input into the fractionation column. That is, adding the operation of the subject invention to an existing fractionation column does not require an increase in the amount of heat which must be supplied by the column's reboiler. For instance on a typical alkylation unit which produces about 11,600 barrels per day (BPD) of motor fuel alkylate the isobutane-rich sidecut vapor stream removed from the isostripper has a flow rate of about 60,000 BPD and a pressure of about 150 psig. In addition a normal butane-rich sidecut stream having a flow rate of about 6,700 BPD is also withdrawn from the isostripper. According to the inventive concept, these streams are depressurized in separate turbines to a pressure near 50 psig and then condensed. The resultant isobutane-rich liquid has a temperature of about 90° F. (38° C.) and is recycled to the reaction zone of the alkylation unit. The power capability of the two turbine generators is approximately 2,060 kilowatts with these two process streams. As used herein, the term "rich" is intended to indicate that a process stream contains at least 55 mole percent of the particular hydrocarbon or class of hydrocarbons which is specified.

To provide a background for the application of the subject invention a brief description of the preferred form of an alkylation process is provided in the following paragraphs. As used herein the term "reaction zone" is intended to indicate a sequence of processing equipment in which the entering reactants are contacted with an alkylation catalyst maintained at alkylation-promoting conditions including one or more reaction vessels and the required equipment for the separation and recovery of the resultant alkylate from process streams recirculated within the reaction zone. It is preferred that the reaction zone contains no fractionation columns other than that used for catalyst regeneration.

The alkylation reaction is promoted by the presence of a mineral acid-catalyst such as hydrofluoric acid, sulfuric acid or phosphoric acid. These acids are preferably maintained in a liquid phase containing a minimum of water to reduce corrosion problems. The maximum amount of water normally allowed in the acid is about 5 wt.%. When fresh acid is charged to a plant, it is normally very dry and contains about 0.5 wt.% water or less. The catalyst may also comprise a mixture of a mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 to about 500 psig, and a more preferred range being from 100 to about 250 psig. It is preferred that the pressure within the reactant-catalyst contacting vessel is approximately 150 psig and essentially "floats" on the pressure maintained in the downstream fractionation zone. Although the desired alkylation reaction may be performed at temperatures from below $-18°$ to about $90°$ C., it is preferred to operate the commercially prevalent isoparaffin-olefin alkylation process in the range of from about $10°$ to about $60°$ C., with $32°$ C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They could however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of venturies or mixing nozzles are often utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into a fractionation column, which is preferably the isostripper column of the subject process. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references and other standard sources.

The net hydrocarbonaceous effluent stream of the alkylation zone is preferably passed into the isostripper column of the motor fuel alkylation unit. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in a $C_4$ alkylation process. A representative set of operating conditions for this column includes an overhead vapor temperature of about $60°$ C. and an overhead pressure of approximately 150 psig. It may contain about 65 actual trays. Preferably the alkylation zone effluent stream enters the isostripper column at an intermediate point. Sidecut streams are preferably removed above and below the feed point. The upper sidecut carried isobutane which has passed through the alkylation zone. Preferably, this isobutane-rich stream is recycled into the alkylation zone. The lower sidecut stream will normally be rich in normal butane and is withdrawn from the alkylation unit. Since it is a lower sidecut stream it will contain some product alkylate. A sidecut stream is by definition removed from an intermediate point in a fractionation column. As used herein the term "intermediate point" is used to indicate a point which is separated from the closest end of the column by at least two actual fractionation trays or an amount of packing equal to at least two theoretical trays.

Propane, including that which is present in the feed stream to the process, will enter the isostripper as part of the alkylation zone effluent stream. The propane is concentrated into the net overhead vapor of the isostripper. The overhead of the isostripper column will also contain HF and isobutane. This net overhead is preferably passed into a second column referred to in the art as a depropanizer in which the isobutane is recovered as a bottoms product. This isobutane is preferably recycled back to the alkylation zone by admixture into the upper sidecut stream of the isostripper. If there is an excess of isobutane in the alkylation unit, this bottoms stream is a good source of high purity isobutane and may be withdrawn from the alkylation zone after being alumina treated. The net overhead of the depropanizer comprises HF and propane and is preferably sent to a third column in which HF is stripped off as an overhead product. The HF may be returned to the alkylation zone and the propane is removed as a net bottoms product and transferred to suitable storage facilities after alumina treatment.

I claim as my invention:

1. In a process for the alkylation of light hydrocarbons having less than six carbon atoms per molecule wherein the light hydrocarbons and an acyclic olefinic hydrocarbon are contacted in the presence of a liquid-phase acid catalyst in a reaction zone, hydrocarbons removed from the reaction zone are separated in a fractionation column operated at a superatmospheric pressure, and a vapor-phase sidecut stream is withdrawn from the fractionation column and subsequently condensed; the improvement which comprises depressurizing the sidecut stream in a power recovery turbine to generate useful energy and then condensing the sidecut stream before recycle of at least a portion thereof to said alkylation reaction zone.

2. In a process for the alkylation of an isoparaffinic hydrocarbon having four or five carbon atoms per molecule wherein the isoparaffinic hydrocarbon and an acyclic olefinic hydrocarbon having less than six carbon atoms per molecule are reacted in a reaction zone in the presence of liquid-phase HF, hydrocarbons withdrawn from the reaction zone are separated in a fractionation column operated at a pressure above about 100 psig, a vapor-phase stream is withdrawn from the fractionation column and subsequently condensed and recycled at least in part to the reaction zone; the improvement which comprises first depressurizing the vapor-phase stream in a power recovery turbine to generate useful energy and then condensing the sidecut stream before recycle of at least a portion thereof to said alkylation reaction zone.

3. The improvement of claim 2 further characterized in that the vapor-phase stream is rich in the isoparaffinic hydrocarbon.

4. The improvement of claim 3 further characterized in that the vapor-phase stream is rich in isobutane.

5. An alkylation process which comprises the steps of:

(a) producing an alkylate hydrocarbon in a reaction zone by reacting an isoparaffinic hydrocarbon having less than six carbon atoms per molecule with an acyclic olefinic hydrocarbon in the presence of an liquid-phase inorganic acid catalyst;

(b) separating a process stream comprising the alkylate hydrocarbon and the isoparaffinic hydrocarbon in a fractionation column operated at a pressure above about 100 psig and thereby producing a net bottoms stream comprising the alkylate hydrocarbon and a vapor-phase sidecut stream which is rich in the isoparaffinic hydrocarbon;

(c) depressurizing the sidecut stream in a turbine and generating useful rotational energy;

(d) condensing the sidecut stream; and, (e) recycling at least a portion of the sidecut stream to the reaction zone.

6. The process of claim 5 further characterized in that the acid catalyst comprises HF.

7. The process of claim 6 further characterized in that the isoparaffinic hydrocarbon is isobutane.

8. The process of claim 7 further characterized in that the olefinic hydrocarbon is a butylene.

9. The process of claim 7 further characterized in that the olefinic hydrocarbon is propylene.

10. The process of claim 7 further characterized in that a second sidecut stream which is rich in a normal paraffinic hydrocarbon is also withdrawn from the fractionation column and is then depressurized through a power recovery turbine and condensed.

11. A motor fuel alkylation process which comprises the steps of:

(a) producing an alkylate hydrocarbon in a reaction zone by the reaction of an isoparaffinic hydrocarbon having less than six carbon atoms per molecule with an acyclic olefinic hydrocarbon in the presence of a catalytically effective amount of HF;

(b) separating a process stream comprising the alkylate hydrocarbon and the isoparaffinic hydrocarbon in a fractionation column operated at a pressure above about 100 psig and thereby producing a net bottoms stream comprising the alkylate hydrocarbon and a vapor-phase stream which is rich in the isoparaffinic hydrocarbon;

(c) depressurizing the vapor-phase stream in a turbine and generating useful rotational energy;

(d) condensing the varpor-phase stream; and, (e) recycling at least a portion of the resultant condensate to the reaction zone.

12. The process of claim 11 further characterized in that the isoparaffinic hydrocarbon and the olefinic hydrocarbon have four carbon atoms per molecule.

* * * * *